United States Patent
Ustuner et al.

(10) Patent No.: US 6,527,720 B1
(45) Date of Patent: Mar. 4, 2003

(54) MEDICAL ULTRASONIC IMAGING METHOD AND SYSTEM FOR SPATIAL COMPOUNDING

(75) Inventors: Kutay F. Ustuner, Mountain View, CA (US); Charles E. Bradley, Burlingame, CA (US); Daniel E. Need, Mountain View, CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/962,965

(22) Filed: Sep. 24, 2001

(51) Int. Cl.⁷ .................................................. A61B 8/00
(52) U.S. Cl. ................................................. 600/443
(58) Field of Search .............................. 600/437, 443, 600/444, 447, 454–458; 73/625–626; 367/7, 11, 130, 138

(56) References Cited

U.S. PATENT DOCUMENTS

| | | | |
|---|---|---|---|
| 5,655,535 A | * | 8/1997 | Friemel et al. ............. 600/443 |
| 5,782,766 A | * | 7/1998 | Weng et al. ................ 600/443 |
| 6,117,081 A | | 9/2000 | Jago et al. |
| 6,126,598 A | | 10/2000 | Entrekin et al. |
| 6,126,599 A | | 10/2000 | Jago et al. |
| 6,135,956 A | | 10/2000 | Schmiesing et al. |
| 6,210,328 B1 | | 4/2001 | Robinson et al. |
| 6,224,552 B1 | | 5/2001 | Jago et al. |
| 6,436,044 B1 | * | 8/2002 | Wang ........................ 600/443 |

* cited by examiner

Primary Examiner—Marvin M. Lateef
Assistant Examiner—Ali M. Imam

(57) ABSTRACT

A medical imaging system provides increased detectability of targets such as membranes, tendons, muscle fibers and biopsy needles that have strong directional responses. This improved result is achieved by compounding multiple images generated by using only one or two transducer firings per ultrasound line. Speckle variance is also reduced as the result of spatial compounding, and this reduction improves the detectability of soft-tissue lesions.

34 Claims, 9 Drawing Sheets

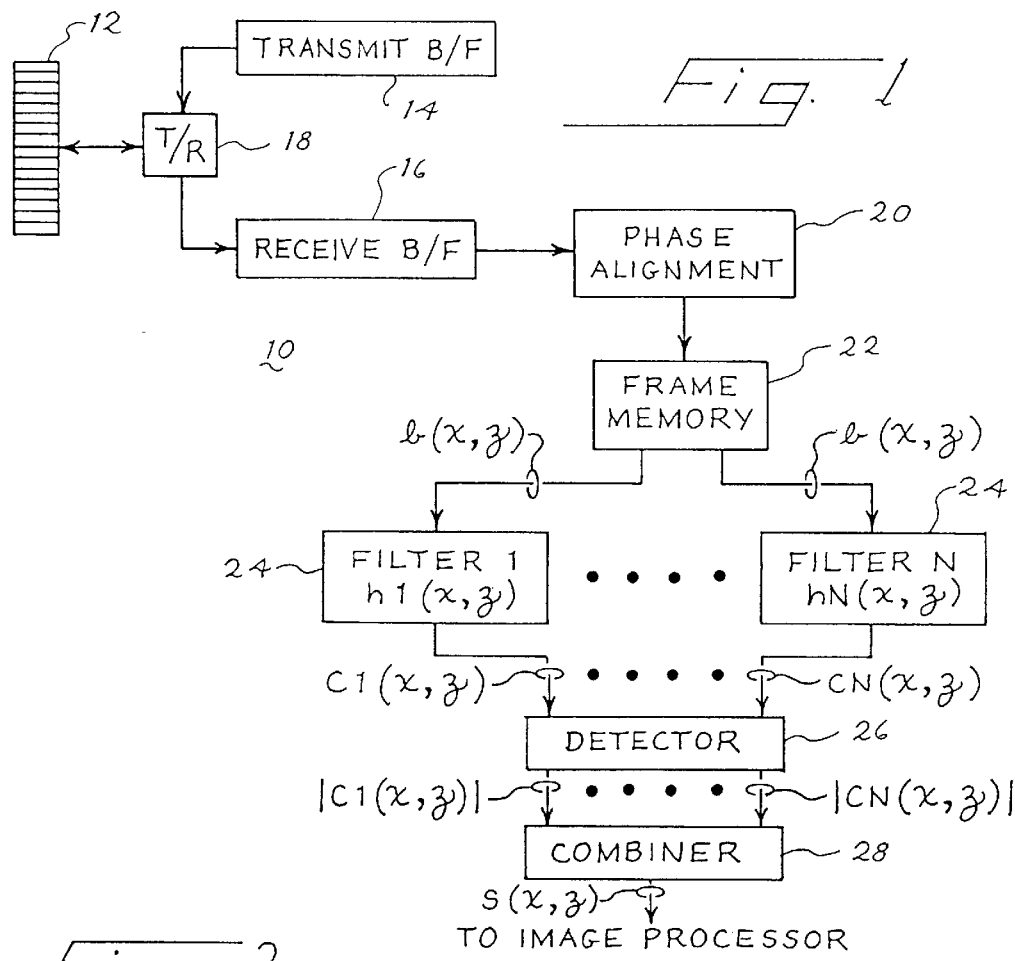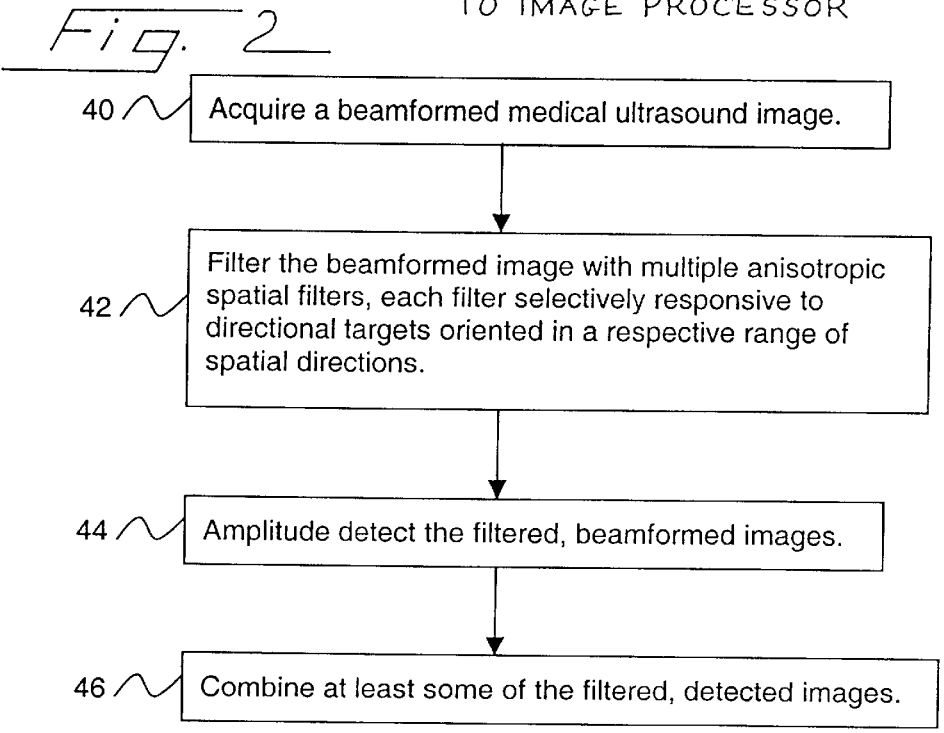

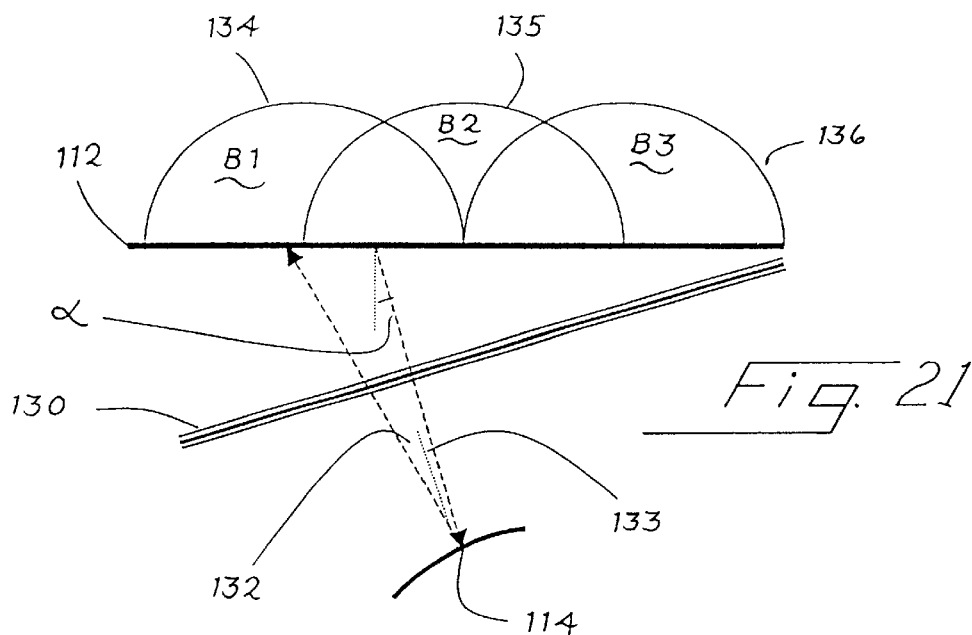
Fig. 21
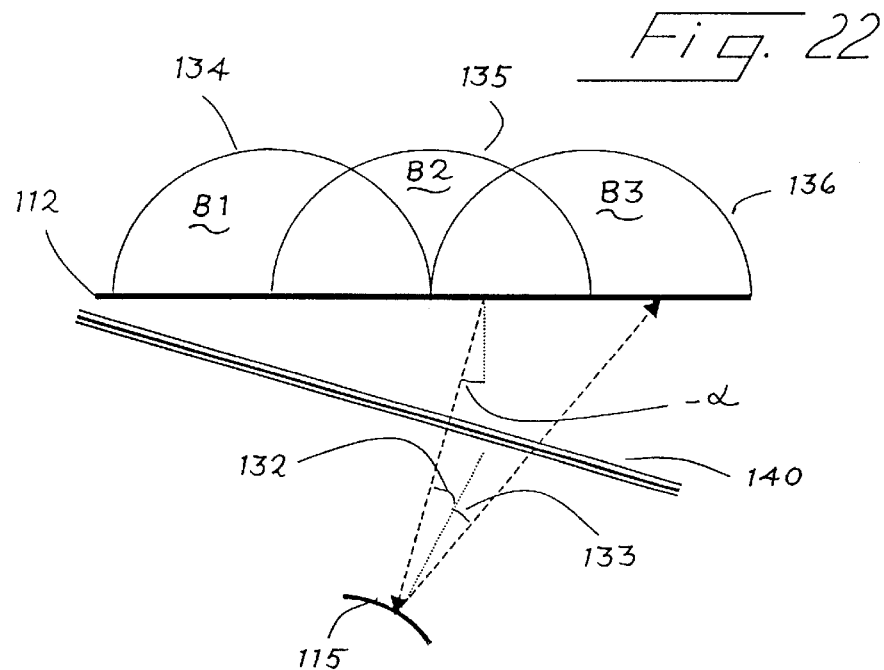
Fig. 22
Fig. 23

MEDICAL ULTRASONIC IMAGING METHOD AND SYSTEM FOR SPATIAL COMPOUNDING

BACKGROUND

The present invention relates to medical ultrasound imaging, and in particular to imaging methods and systems that provide improved imaging of directional targets.

Objects of interest for medical ultrasonic imaging include resolvable targets with strong directionality such as membranes between different types of soft tissue, ducts, tendons, muscle fibers, and interventional devices such as biopsy needles. In general, objects with substantially planar or linear acoustic impedance boundaries within the round-trip sample volume of an imaging system behave as directional acoustic targets. They do not scatter incident sound waves isotropically, but reflect them back anisotropically such that the reflection angle with the surface/line normal is equal to the incidence (insonification) angle (Snell's Law). For this reason, such directional targets locally have a narrow spatial or lateral bandwidth. If the imaging system spatial impulse response has a narrow bandwidth, i.e. the range of incidence angles is narrow and the receiver is responsive to substantially the same range of angles, directional targets will often not be detected when the incidence angle is substantially different from zero. On the other hand, if the system spatial impulse response has a wide bandwidth, i.e. the insonification subtends a wide range of angles and the receiver is responsive to echoes from a wide range of angles, then the signal-to-noise ratio (SNR) of the narrow bandwidth signals (e.g., reflections from a directional target) are compromised. In either case the detectability of directional targets may be significantly reduced.

One prior-art technique that improves the detectability of directional targets is spatial compounding, where the target is imaged multiple times from substantially different angles and the images are then combined after amplitude detection (Jago U.S. Pat. No. 6,126,599 and Schmiesing U.S. Pat. No. 6,135,956). With the conventional spatial compounding technique, however, the temporal resolution is sacrificed because of multiple firings needed for each frame of compounded image (Entrekin U.S. Pat. No. 6,126,598 and Robinson U.S. Pat. No. 6,210,328). The temporal resolution loss can be unacceptably high for applications that require high temporal bandwidth, or for applications that inherently have low frame rates, e.g., 4-D imaging. The conventional spatial compounding technique also suffers from motion artifacts if the transducer or object is in motion during the acquisition of component image frames (Jago U.S. Pat. No. 6,117,081). Images with conventional spatial compounding can also exhibit seam artifacts at the borders of component image frames (Jago U.S. Pat. No. 6,224,552). Thus, a need presently exists for an improved method for imaging directional targets that has a reduced adverse effect on the frame rate, reduced motion artifact and reduced discontinuities in the compound frame.

SUMMARY

The methods and systems described below improve the contrast resolution of medical ultrasound images, particularly when directional targets of the type described above are imaged. The disclosed systems compound multiple images that are generated using only a single firing per ultrasound line or in some cases two firings per ultrasound line. Speckle variance is also reduced as a natural result of spatial compounding, and this further improves the detectability of soft-tissue lesions.

One system described below uses a bank of anisotropic band-pass filters prior to amplitude detection to create multiple component images. The other system creates multiple receive beams from a single weakly diverging, planar, or weakly focused transmit beam by using partially overlapping receive sub-apertures. Both the filtered images of the first system and the sub-aperture receive beams of the second system are selectively sensitive to directional targets oriented in respective ranges of angular positions. When the filtered component images (in the first system) or the sub-aperture receive beams (in the second system) are combined after detection, the desired improved imaging of directional targets is obtained. The first system preserves the frame rate and the second system allows spatial compounding with improved frame-rates. Therefore these systems address the temporal resolution loss issues of conventional spatial compounding and consequently provide reduced motion artifact.

The foregoing paragraphs have been provided by way of general introduction, and they should not be used to narrow the scope of the following claims.

BRIEF DESCRIPTION OF THE DRAWINGS

FIG. 1 is a block diagram of a medical ultrasonic imaging system that incorporates a first preferred embodiment of this invention.

FIG. 2 is a block diagram of a method implemented by the system of FIG. 1.

FIGS. 19–23 are schematic diagrams illustrating various modes of operation of the system of FIG. 17.

DETAILED DESCRIPTION OF THE DRAWINGS

Figure 3:
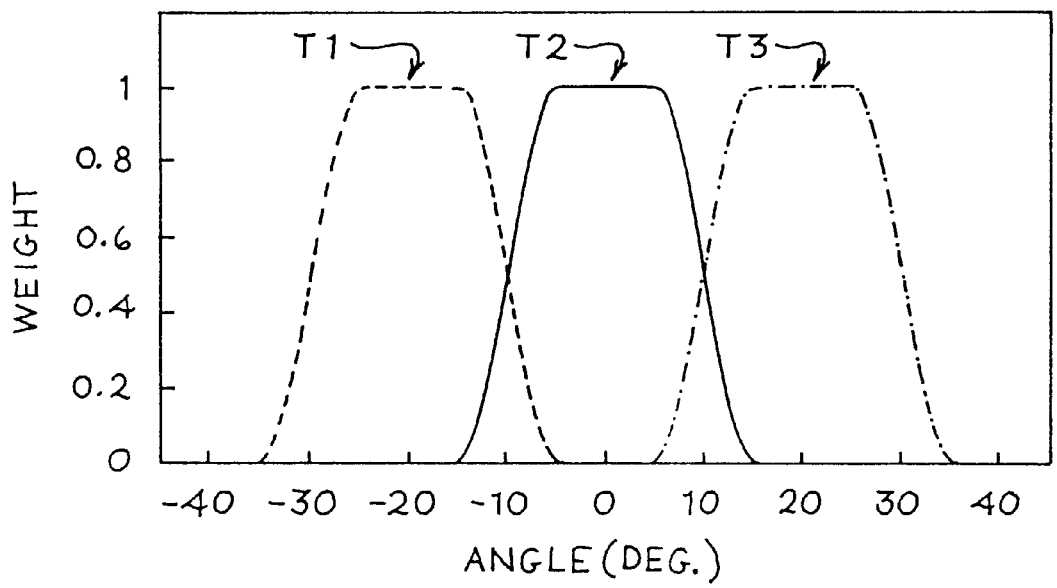
FIGS. 3 and 4 show the angular and temporal frequency responses, respectively, of a bank of anisotropic pre-detection filters for a three-way spatial compounding example.

Turning now to the drawings, FIG. 1 is a block diagram of an ultrasonic imaging system 10 that incorporates a first preferred embodiment of this invention. The system 10 includes a transducer array 12 that is coupled to both a transmit beamformer 14 and a receive beamformer 16 by a transmit/receive switch 18.

The elements 12–18 can be conventional systems. The transducer array 12 can be a 1, 1.25, 1.5, 1.75, 2, or 3-dimensional array. By way of example, the transducers described in the following patents (all assigned to the assignee of the present invention) can readily be adapted for use with this invention: U.S. Pat. Nos. 5,261,408; 5,297,533; 5,410,208; 5,415,175; 5,438,998; 5,562,096; 5,657,295; 5,671,746; 5,706,820; 5,757,727; 5,792,058; 5,916,169; 5,920,523. This list is not intended to be limiting, and any suitable transducer array can be used.

Similarly, a wide variety of analog and digital techniques can be used to implement the transmit beamformer 14 and the receive beamformer 16 (on occasion referred to as the transmitter and the receiver, respectively, in this specification). The following U.S. Patents, all assigned to the assignee of the present invention, provide examples of the types of approaches that can be used to implement the transmit beamformer 14: U.S. Pat. Nos. 4,550,607; 4,699,009; 5,148,810; 5,608,690; and 5,675,554. The following U.S. Patents, also all assigned to the assignee of the present invention, provide examples of the types of approaches that can be used to implement the receive beamformer 16: U.S. Pat. Nos. 4,550,607; 4,699,009; 5,555,534. These examples are, of course, not intended to be limiting in any way, and it should be understood that the receive beamformer 16 can perform the appropriate delay, phase adjustment and apodization in either the time domain or the frequency domain.

The receive beamformer 16 generates receive beams along selected receive directions, and these receive beams are applied to a phase alignment system 20. The phase alignment system 20 corrects phase misalignment between laterally adjacent samples in the receive beams. Such phase misalignment may result from system-related factors such as scan geometry, physical aperture limitations and the like. Any suitable system can be used to perform the desired phase adjustment, including the systems described in the following U.S. Patents, assigned to the assignee of the present invention: U.S. Pat. Nos. 5,928,152, 5,921,932. For some scan geometries (such as the sector scan geometry) and some imaging systems, phase misalignment may not be a problem and the system 20 may not be needed.

The phase-aligned receive beams generated by the phase alignment system 20 are applied to a frame memory 22, which stores two or more phase-aligned receive beams. In one example, the frame memory stores all or part of a frame.

A bank of filters 24 is provided, and each of the filters 24 is coupled with the frame memory 22. In this embodiment, each of the filters 24 is a respective anisotropic spatial band-pass filter that filters at least in the lateral direction (across receive beams). For example, each filter 24 may be a respective lateral or a respective 2-dimensional filter. The filters 24 can operate in the spatial domain or in the spatial frequency domain. Any pre-detection line or range interpolation is preferably deferred until after the images have been filtered with the filters 24 for reasons of efficiency.

The filtered and interpolated images from the filters 24 are applied to an amplitude detector 26, and the detected images are applied to a combiner 28.

The samples of the beamformer output, impulse response of the filters 24, and output of the filters 24 are defined in the axial (range) z axis and at least one of the lateral axes, azimuth x and elevation y. Note that x, y and z in this example are the axes of the acoustic grid and not necessarily the axes of the Cartesian coordinate system, because the filtering and compounding preferably take place before scan conversion.

In the following we will describe a 2-D spatial compounding technique, where one of the axes is the axial and the other one is a lateral (azimuth or elevation) axis. 3-D spatial compounding is a straightforward extension of the 2-D technique described below.

Spatial Compounding Using Spatial or Frequency Domain Filtering

The spatial domain filtering for 2-D spatial compounding is a 2-D convolution of the phase-aligned beamformer output $b(x, z)$ with the 2-D impulse response $h(x, z)$ of an anisotropic filter 24.

As an example, 2-D two-way compounding (compounding with two 2-D component images) in the spatial domain can be described as follows:

$c_1(x, z) = b(x, z) * h_1(x,z)$, $c_2(x,z) = b(x,z)\ h_2(x,z)$, $d(x, z) = g(|c_1(x, z)|, |c_2(x, z)|, |b(x, z)|)$, where * is the 2-D convolution operation in x and z, $h_1$ and $h_2$ are the impulse responses of anisotropic filters with partially overlapping or nonoverlapping pass bands, $c_1$ and $c_2$ are the filtered component images, $g(.)$ is a compounding function, $|.|$ is the magnitude function, and $d(x, z)$ is the compounded image. As indicated here, the compounding function $g(.)$ may also be a function of the input image (beamformer output) in addition to being a function of the component images.

The frequency domain filtering for 2-D spatial compounding, on the other hand, is a multiplication of the two-dimensional Fourier transform $B(f_x, f_z)$ of the phase-aligned beamformer output $b(x, z)$ with the two-dimensional Fourier transform $H(f_x, f_z)$ of the impulse response $h(x, z)$ of an anisotropic filter 24.

As an example, two-way compounding in the spatial frequency domain can be described as follows:

$C_1(f_x, f_z) = B(f_x, f_z)\ H_1(f_x, f_z)$, $C_2(f_x, f_z) = B(f_x, f_z)\ H_2(f_x, f_z)$, $c_1(x, z) = F^{-1}\{C_1(f_x, f_z)\}$, $c_2(x, z) = F^{-1}\{C_2(f_x, f_z)\}$, $d(x, z) = g(|c_1(x, z)|, |c_2(x, z)|, |b(x, z)|)$, where, B, $H_1$ and $H_2$ are the 2-D Fourier transforms of the phase-aligned beamformer output $b(x, z)$ and the impulse responses $h_1(x, z)$ and $h_2(x, z)$ of the anisotropic filters 24, respectively; $f_x$ is the lateral spatial frequency and $f_z$ is the axial spatial frequency; $C_1$ and $C_2$ are the Fourier transform of the component images $c_1$ and $c_2$; and $F^{-1}\{.\}$ indicates a two-dimensional inverse Fourier Transform.

Anisotropic Filter Impulse Response

The spatial domain impulse response $h(x, z)$ of an anisotropic filter 24 can be derived by the linear superposition of plane waves where each plane wave is weighted by the desired angular and temporal frequency weight.

$$h(x, z) = \int\int G(\theta, f) e^{j2\pi \frac{f}{(c/2)}(\sin(\theta)x + \cos(\theta)z)} f\, df\, d\theta$$

where $G(\theta,f)$ is the angular and temporal frequency weight of a plane wave (the exponential term) having a steering angle $\theta$ and a temporal frequency f. The round-trip speed of sound in the medium is $c/2$, where c is the one-way speed of sound. In general $G(\theta,f)$ can be an arbitrary complex function of $\theta$ and f.

In the preferred embodiment, G is a separable function of $\theta$ and f, i.e., $G(\theta,f) = T(\theta)\ S(f)$. Therefore, $$h(x, z) = \int T(\theta) \int S(f) e^{j2\pi \frac{f}{(c/2)}(\sin(\theta)x + \cos(\theta)z)} f \, df \, d\theta$$

where $T(\theta)$ is the angular response, $S(f)$ is the round-trip temporal frequency response. $T(\theta)$ can be selected to maximize SNR (i.e., detectability) of a particular anisotropic target by matching $T(\theta)$ to the angular response of the target (matched-filter). $T(\theta)$ can also be designed to compensate for the angular response of the imaging system 10 (Inverse Filter or Wiener Filter). $S(f)$ can be selected to preserve the input temporal spectrum (a band-pass or an all-pass filter), or alternatively it can be selected to provide additional filtering (e.g., Matched Filter, Inverse Filter, Wiener Filter, etc.). Note that even though $G(\theta,f)$ is a separable function of $\theta$ and $f$, the resultant filter impulse response $h(x, z)$ in general is not a separable function of x and z, i.e., it can not be written as the multiplication of a function of x and a function of z.

Anisotropic Filters for Spatial Compounding

In the preferred embodiment, the angular weighting functions $T_i(\theta)$, i=1:N, of the anisotropic filters 24 are chosen such that they partially overlap in $\theta$ covering the full angular (lateral) spectral width of the beamformer output from $\theta_{min}$ to $\theta_{max}$, $S(f)$ on the other hand is selected to preserve the input temporal response. Therefore, if the beamformer output is an Intermediate Frequency (IF) or Radio Frequency (RF) signal, $S(f)$ is preferably the frequency response of a wide-band band-pass filter. If the beamformer output is a base-band analytic signal, then $S(f)$ is preferably the frequency response of a wide-band low-pass filter. However, if the same filter bank is expected to perform additional functions other than generating the component images for spatial compounding, such as whitening, then $S(f)$ may take other shapes.

The number of lateral sub-bands N and/or the type of the angular weighting function $T_i(\theta)$ can be varied dependent on the clinical application, e.g., abdomen, OB, breast, musculoskeletal, etc. $S_i(f)$ can be a function of the corresponding $T_i(\theta)$. For example, the upper band edge of the band-pass temporal frequency response $S_i(f)$ can be shifted down as the absolute value of angle $|\theta|$ increases in order to reduce grating lobes. The shape of the angular and the temporal frequency responses can also be selected independently. The shape can be Gaussian, RECT, triangular or any other arbitrary shape. However, to keep the side-lobes and range-lobes of the filter's spatial impulse response low, the angular and temporal frequency responses are preferably smooth in their pass band and tapered at the edges.

$T_i(\theta)$ and $S_i(f)$ can also be adaptive. For example, the number of angular sub-bands N, and therefore the angular width of each sub-band, can be adaptive to the pixel or local Coherence Factor. The coherence factor is the ratio of the coherent (phase-sensitive) summation to the incoherent (phase-insensitive) summation of the delayed and apodized signals of the receive channels. The local Coherence Factor is the pixel Coherence Factor averaged over an area around each pixel. The number of angular sub-bands N can be reduced as the Coherence Factor increases. Similarly, $S(f)$ can be adaptive to the pixel or local SNR in that it can be selected to be a Wiener Filter if the SNR is high or a Matched Filter if the SNR is low.

Figure 4:
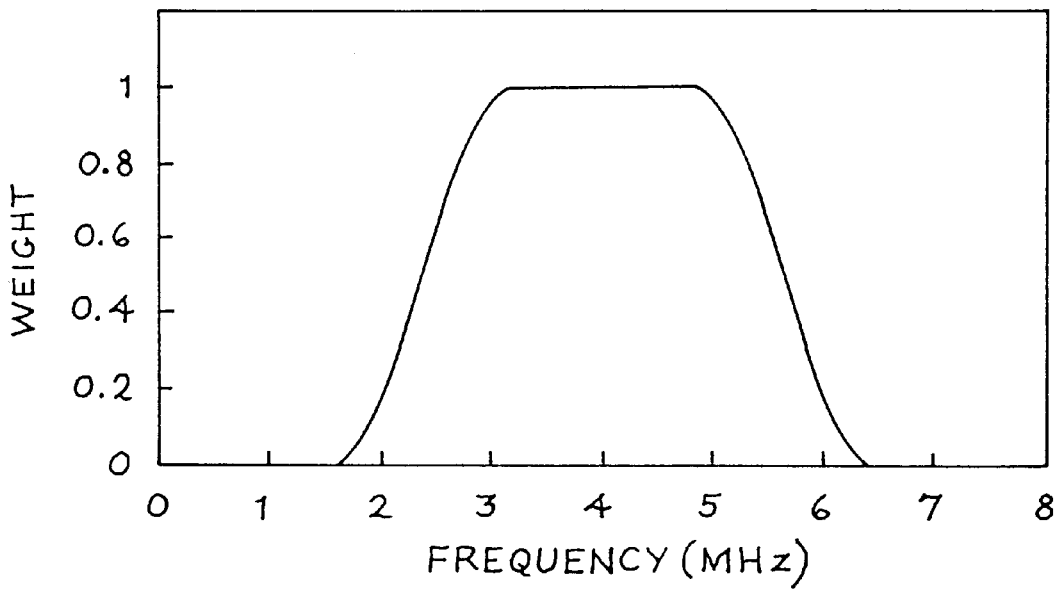

FIGS. 3 and 4 show the angular and temporal frequency responses, respectively, of a set of anisotropic filters 24 $h_i(x,z)$, i=1:3, for a three-way compounding example. The respective angular responses $T_i(\theta)$, i=1:3, are flat-top, Cosine-Taper in shape and have the same −6 dB angular width of 20°. The center angles of the filters are −20°, 0° and +20°, respectively. The assumption here is that the beamformer output has angular frequency components ranging from −30° to +30°, i.e., $\theta_{min}$=−30° to $\theta_{max}$ =30°. The temporal frequency responses are the same for all three filters, $S_i(f)$=$S(f)$, i=1:3, and $S(f)$ is a band-pass filter with a flat-top, Cosine-Taper pass band.

Figure 5:
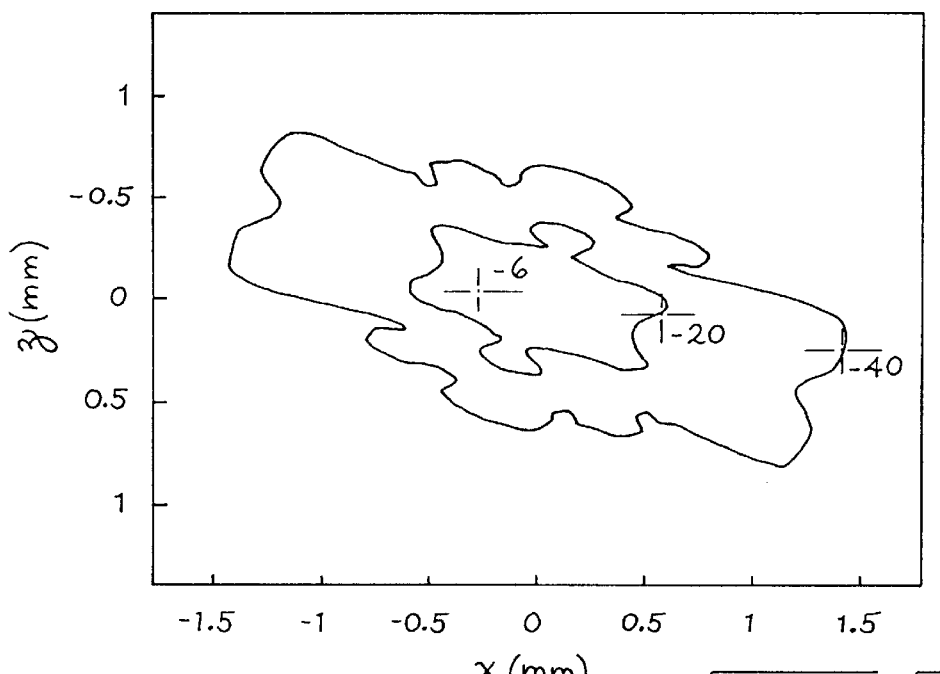
FIGS. 5, 6 and 7 show contour plots of the magnitude of the spatial impulse response of the filters of FIG. 3.
Figure 6:
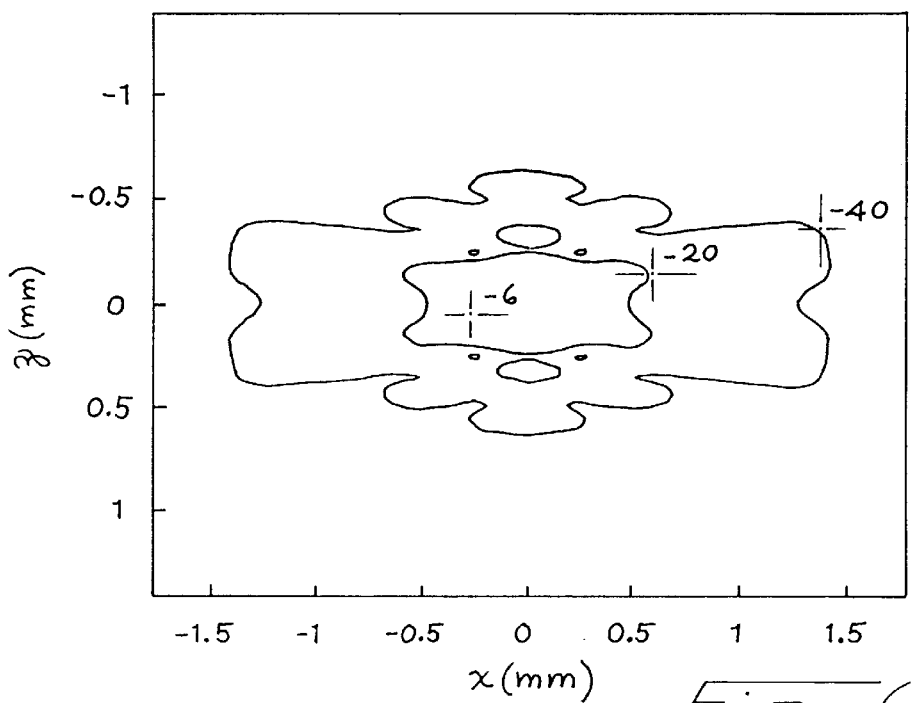
Figure 7:
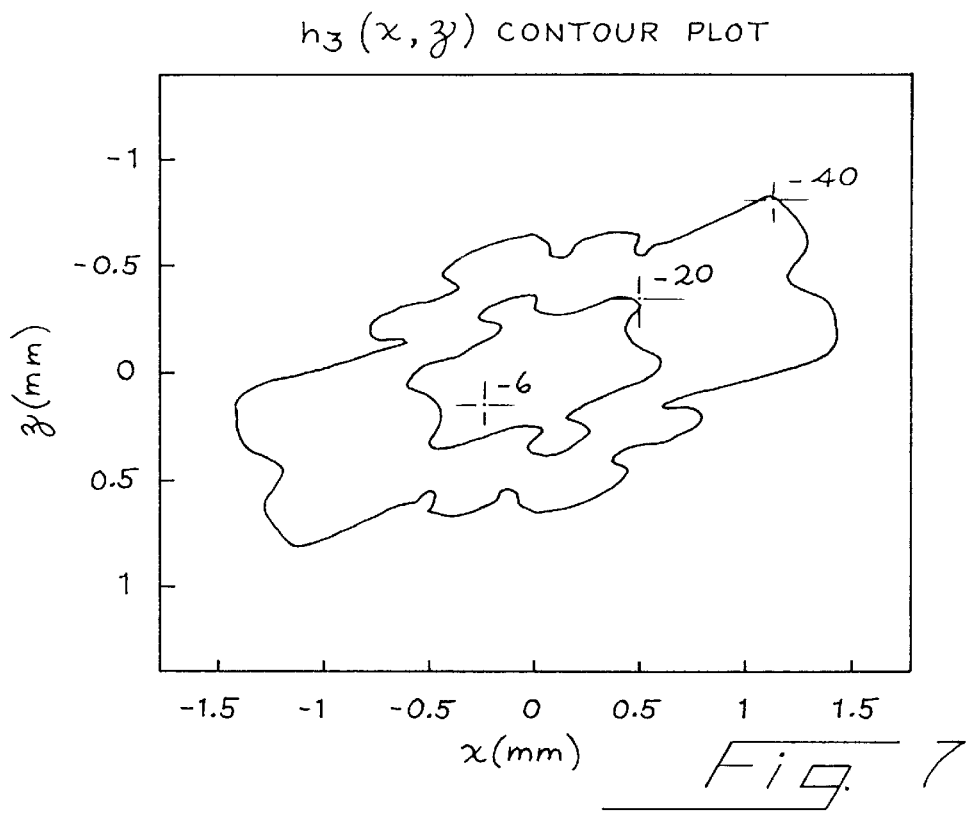

FIGS. 5, 6 and 7 respectively show the contour plots of $|h_i(x,z)|$, i=1:3, where $|.|$ is the magnitude operator. The axes of the contour plots are the lateral x and axial z dimensions. Note that the filters are complex, and they are therefore fully defined by the magnitude and phase, or the real and imaginary parts of the impulse response. The equi-phase lines of an anisotropic filter impulse response are substantially at normal angle to the center angle axis.

Figure 8:
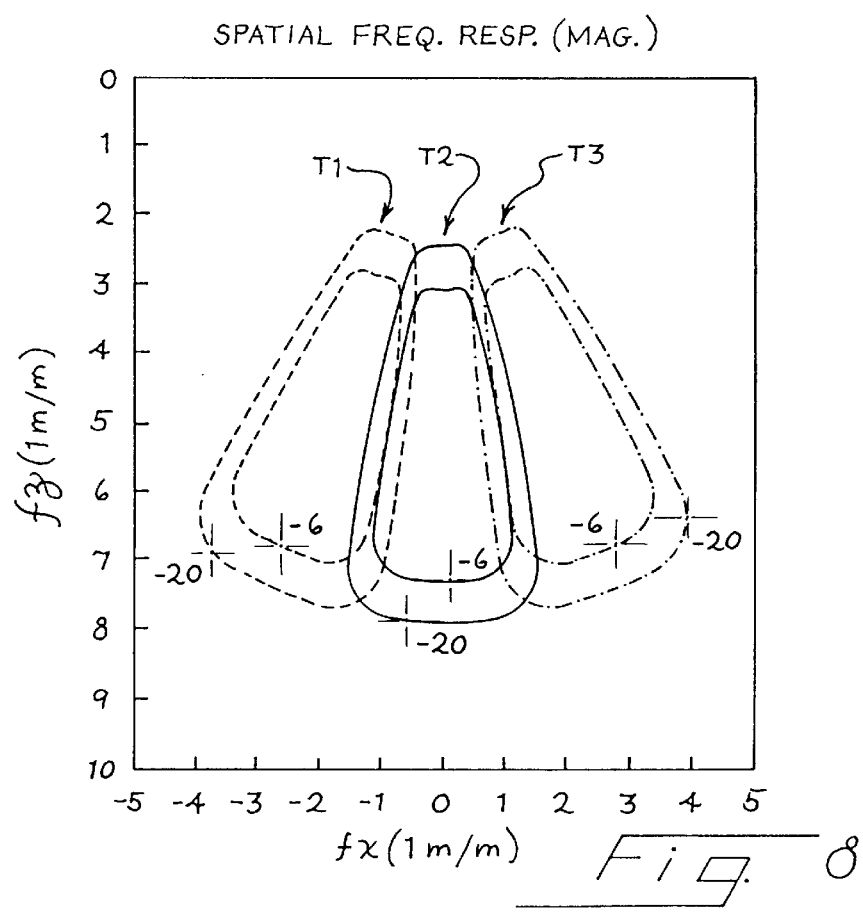
FIG. 8 shows the contour plots of the magnitude of the spatial frequency spectra of the filters of FIG. 3.

FIG. 8 shows the −6 and −20 dB contour plots of the spatial frequency spectra $H_i(f_x, f_z)$, i=1:3 (i.e., 2-D Fourier Transform of $h_i(x, z)$, i=1:3). The axes are the lateral spatial frequency $f_x$ and axial spatial frequency $f_z$.

Compounding Function

The combiner 28 for both the spatial domain and the spatial frequency domain embodiments can use various compounding functions. The most general form of the combiner is $d(x, z)=g(c_1(x, z),c_2(x, z), \ldots, c_N(x, z),b(x, z))$, where $g(.)$ is a multi-input, single-output compounding function (map). The compounding function may include a nonlinear relationship between one or more of its inputs and the output. The inputs of the compounding function may also include the beamformer's output $b(x, z)$. The compounding may also be dependent on the local statistics such as the local average of the magnitude of $c_i(x, z)$ and/or $b(x, z)$.

Some examples of compounding functions are as follows:
a) Log Domain Compounding
  $d(x, z)=\Sigma_{i=1:N} \alpha_i \, 10 \, \log_{10}(|c_i(x, z)|^2)$,
b) Intensity Domain Compounding
  $d(x, z)=10 \, \log_{10}(\Sigma_{i=1:N} \alpha_i \, |c_i(x, z)|^2)$
c) MAX Compounding
  $d(x, z)=10 \, \log_{10}(\max_{i=1:N}\{|c_i(x, z)|^2\})$,
where $\max\{.\}$ is the maximum operator.

The parameter $\alpha_i$ in examples (a) and (b) above is the weighting coefficient for the $i^{th}$ filter's output and it is typically set to $1/N$. $\alpha_i$ may also be adaptive to, for example, the pixel or local Coherence Factor, or the pixel or local SNR of the map's input images. $\alpha_i$ may also be used to compensate for the element factor of the transducer elements. The spatial frequency spectrum of the element factor is dominated by a lateral Sinc function (Sinc(w $f_x$)) that has its first zeros at $f_x$=±$1/w$, where w is the effective element width along the x axis. The compounding function itself may also be varied within the same compounded frame. The variation can be adaptive to the pixel or local Coherence Factor, or the pixel or local SNR of the component images $c_i(x, z)$, i=1:N.

Operation

FIG. 2 provides a flowchart of a method implemented by the system 10 of FIG. 1. In block 40 an ultrasound image is acquired. Such an image may for example be an image stored in the frame memory 22 of FIG. 1.

In block 42 a given image is filtered with multiple band-pass filters to create multiple filtered images prior to amplitude detection. Each filter is selectively responsive to directional targets oriented in a respective range of spatial directions. As pointed out above, the band-pass filters can operate in the spatial domain or the spatial frequency domain, and the filters can include lateral one-dimensional, two-dimensional and three-dimensional filters. The filtered images are then amplitude detected in block 44, and at least some of the filtered, detected images are combined in block 46.

The combining act of block 46 represents a type of spatial compounding. Because the filters used in block 42 are selectively responsive to respective directional targets, the compounding of block 46 achieves the desired result of enhancing the image of such directional targets. The compounded image produced in block 46 is then applied to an image processor.

Alternatively the combining act may include the human observer. For example a two-way compounding operation may consist of applying the left and right component images (directly or after a 3-D specific processing) respectively to the left and right eyes of the observer. The human brain will then perform the combining operation of the compounding. This may help 3-D visualization of the anatomy if a 2-D array is used. Another alternative is a hybrid approach where some combining takes place in the imaging system and the rest in the human brain.

A Particular Implementation with Three Component Images

For the general 2-D case, each filter 24 in the bank of anisotropic filters 24 will require inseparable 2-D convolution. Alternatively, it may be more efficient to implement the filters in the frequency domain. The associated processing, as discussed above, includes a Fourier transform of the input signal, as well as an inverse Fourier transform of the component images. For example, spatial compounding based on three component images can be performed with four Fourier transform operations, or three convolution operations.

Figure 9:
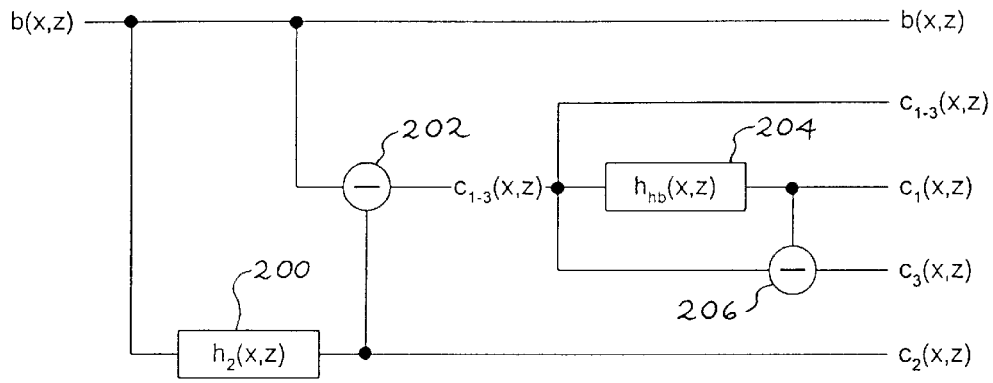
FIG. 9 is a block diagram of a system for implementing the bank of filters 24 of FIG. 1.
Figure 10:
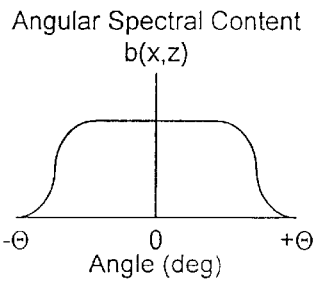
FIGS. 10–14 are angular spectral content graphs for five of the signals of FIG. 9.
Figure 11:
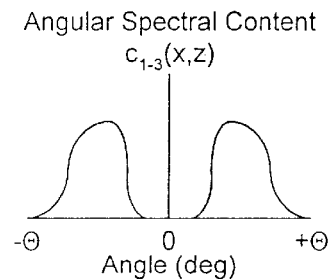
Figure 12:
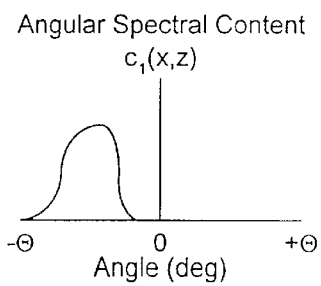
Figure 13:
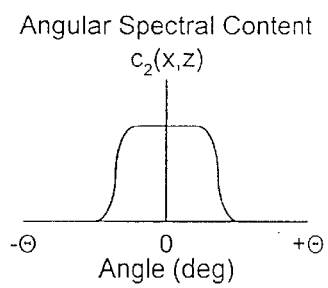
Figure 14:
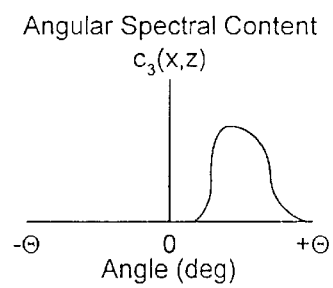

When the requirements of the application are met by compounding with three component images, separated from other requirements such as adaptive filtering or whitening, the architecture can leverage the symmetries in the signal processing to achieve significant simplification in filter bank complexity. One such approach is illustrated in FIG. 9. This architecture for a filter bank produces three sub-band component images, with only a single inseparable filtering operation. The following discussion assumes a hardware implementation of the signal processing, but similar considerations apply to a software approach, whether on a general-purpose CPU or a dedicated DSP.

In the system of FIG. 9, the input image, $b(x,z)$, is filtered through an anisotropic spatial filter in block 200. This filter is constrained to an angular frequency response that is symmetric about 0°, such as the angular response T2 of FIG. 3. The output of this filter, $c_2(x,z)$, is the component image for the center spatial frequency band.

The original input image, $b(x,z)$, and the center component image, $c_2(x,z)$, are used to generate the component images for lateral spatial frequency bands. First, in subtractor 202, the center component image is subtracted from the input image. This results in $c_{1-3}(x,z)$, which is a component image consisting of the left and right spatial frequency bands. This may be of use directly, or can be further separated by applying a half-band filter, block 204, which generates $c_1(x,z)$. The final sub-band component image $c_3(x,z)$ is generated by taking the difference of $c_{1-3}(x,z)$ and $c_1(x,z)$ in subtractor 206.

FIGS. 10–14 display a representation of how the spectral content of the signals throughout processing of FIG. 9 may look. Clearly, the actual spectra depend primarily on the input signal spectrum and the design of the filter $h_2(x,y)$ of FIG. 9.

The value of this architecture is that it is possible to implement the entire bank of anisotropic filters with a single programmable function. The rest of the signal processing can be implemented with fixed processing, relying primarily on the simple arithmetic functions of addition and subtraction. The cost and complexity is collected in the single anisotropic filter 200 of FIG. 9. This filter is defined in such a way as to allow even further simplification.

The symmetry conditions on the filter frequency response leads to even symmetry in Fx, and therefore even symmetry in x for the tap weights of an FIR filter core. Such a filter can be implemented by convolution with only one half of the multipliers that would be required for an asymmetric filter of the same complexity.

Alternatively, the function of block 200 can be implemented in the spatial frequency domain, as suggested above. This may be appropriate, given the computational efficiency of FFT algorithms. Should such an approach be chosen, only two Fourier transform operations are used, instead of the four suggested previously.

The complexity in the generation of $c_1(x,z)$ and $C_3(x,z)$ lies in the filter $h_{hb}(x,y)$ of FIG. 9. This filter, however, is separable in Fx and Fz, and is all-pass in Fz. That is, it is only a lateral filter that to separates positive frequencies from negative frequencies. Standard simplification approaches exist for efficient half-band filter implementation. One possibility is to apply an FIR half-band filter, which can be constrained to have all of the even coefficients set to 0. While the coefficients will be complex, the number of complex multipliers will still be one half of the effective number of taps. Another possibility is to employ the Hilbert transform to separate the positive and negative frequencies. Regardless of the approach, the function can easily be implemented in fixed hardware with no programmability.

This discussion has assumed that the filtering and compounding operations are applied on full images. However, the approach is general, and can also be applied to sub-sets of the image. The choice of full images or sub-sets of the images will often depend on the architectural capabilities of the ultrasound system.

A Particular Implementation with Uniform Component Bands

The previous implementation leveraged a single complex, non-separable 2-D filter to generate three component images. It is also possible to use a single complex, non-separable 2-D filter to deliver an arbitrary number of component images, under the constraint that pass bands vary only in the center angular frequencies.

Figure 15:
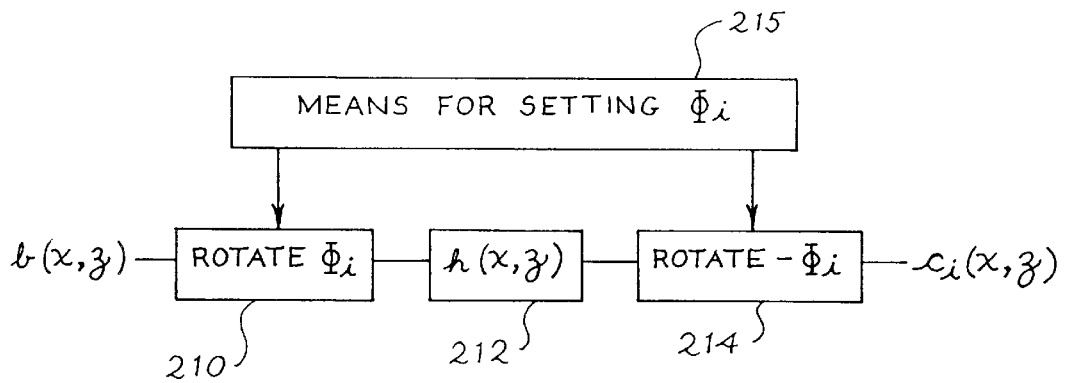
FIG. 15 is a block diagram of another system for implementing the bank of filters 24 of FIG. 1.

This type of filter bank is diagrammed in FIG. 15. The input image signal $b(x,z)$ is first rotated by an angle $\Phi_i$ by rotator 210, and then filtered by the anisotropic spatial filter 212. The filtered output is further rotated by the negative angle $-\Phi_i$ in counter rotator 214, producing a single component image. This operation can be repeated any number of times with unique rotations as successively selected by the block 215, thereby producing as many component images as desired. The implementation may use the same rotation and filter engine multiple times on buffer images, or alternatively, may include multiple instances of the engine which operates on the same image in parallel.

Figure 16:
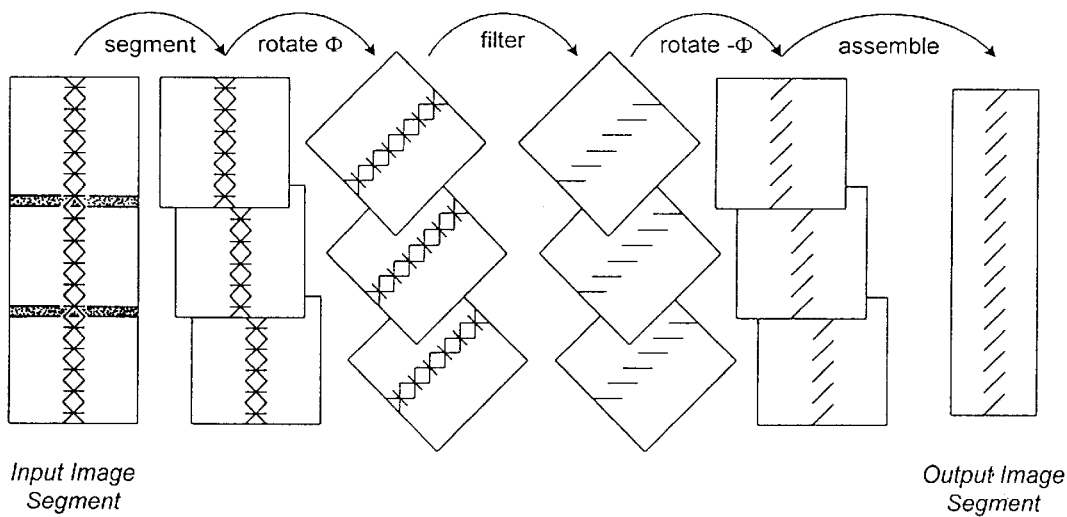
FIG. 16 is a schematic diagram illustrating operation of the system of FIG. 15.

FIG. 16 further illustrates this architecture by considering the selection of the image components of a single angular orientation. In this example, the input image is segmented for processing and then re-assembled to generate the component image. This sequence is repeated for each angular orientation and component image.

The value of this architecture is again that it can leverage a single complex non-separable 2-D filter. As described previously, the filter itself may be implemented by convolution or Fourier transform techniques.

Second Preferred Embodiment

Figure 17:
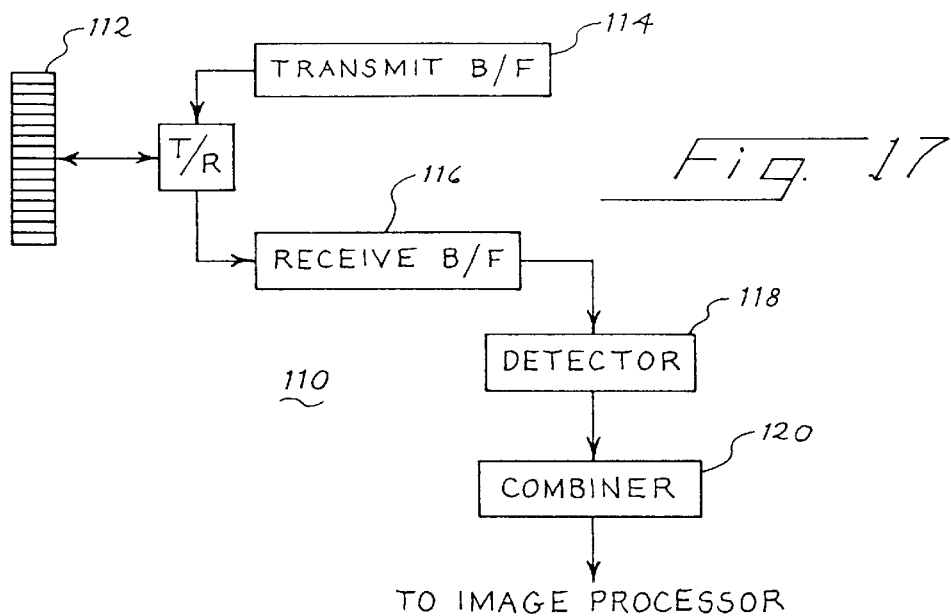
FIG. 17 is a schematic diagram of a medical ultrasonic imaging system that incorporates a second preferred embodiment of this invention.

The embodiment of FIGS. 17–23 also enhances imaging of directional targets, without requiring the pre-detection filters of the system 10. FIG. 17 shows a block diagram of an ultrasonic imaging system 110 that includes an array 112, a transmit beamformer 114, and a receive beamformer 116. The elements 112, 114, 116 may correspond to the elements 12, 14, 16 described above.

The receive beamformer 116 performs the appropriate delay, phase adjustment, and apodization in either the time domain or the frequency domain. The receive beamformer can be a conventional parallel beamformer that can, using a single receive data set, form multiple beams with partially overlapping apertures along an ultrasound line. Alternatively, it can be a beamformer that can, using a single receive data set, form multiple beams for each acoustic or display grid point within the insonification area/volume. This beamformer can achieve very high frame rates if the insonification area/volume per transmit firing is wide/big as in the case of weakly diverging, planar or weakly focused transmit waves. A few firings would then be sufficient to form a spatially compounded image frame or image volume. However, this beamformer requires much higher processing bandwidth and storage capacity than conventional beamformers. Also achieving clinically acceptable clutter levels may require special measures because of transmit beams being unfocused or weakly focused. See U.S. patent application Ser. No. 09/518,972 (assigned to the assignee of the present invention and hereby incorporated by reference in its entirety) for further details.

The receive beams generated by the receive beamformer 116 are applied to an amplitude detector 118, and selected ones of the detected beams are combined in a combiner 120.

Figure 18:
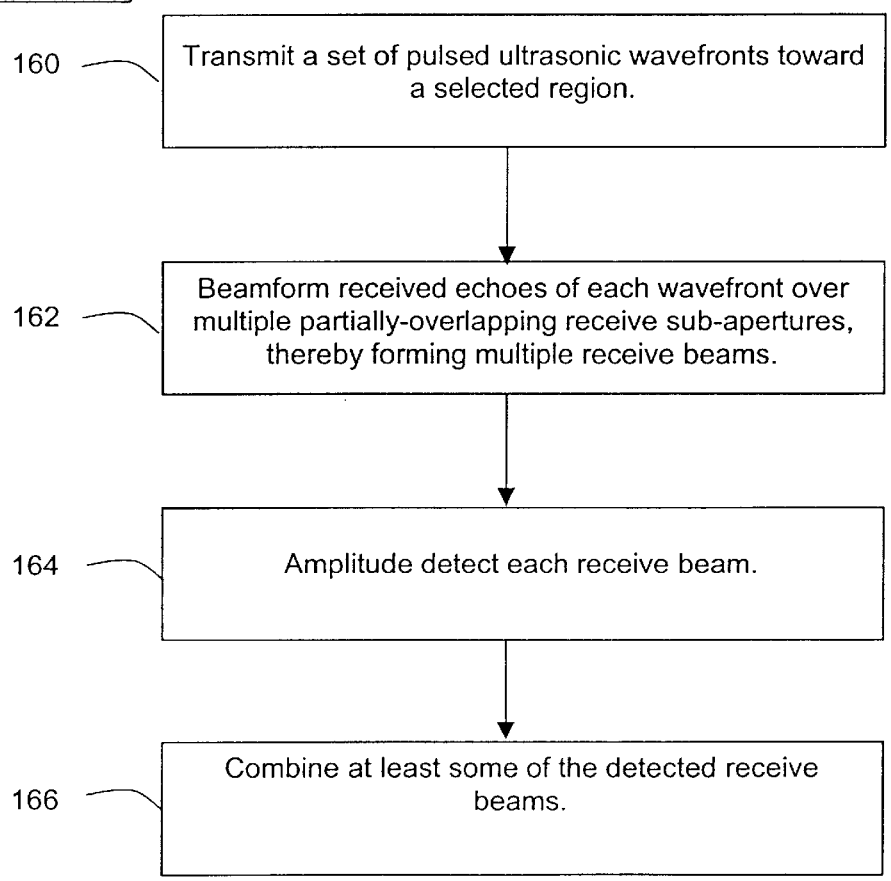
FIG. 18 is a block diagram of a method implemented by the system of FIG. 17.

FIG. 18 provides a block diagram of a method implemented by the system 110. In block 160, a set of pulsed ultrasonic wavefronts is transmitted toward a selected region.

Figure 19:
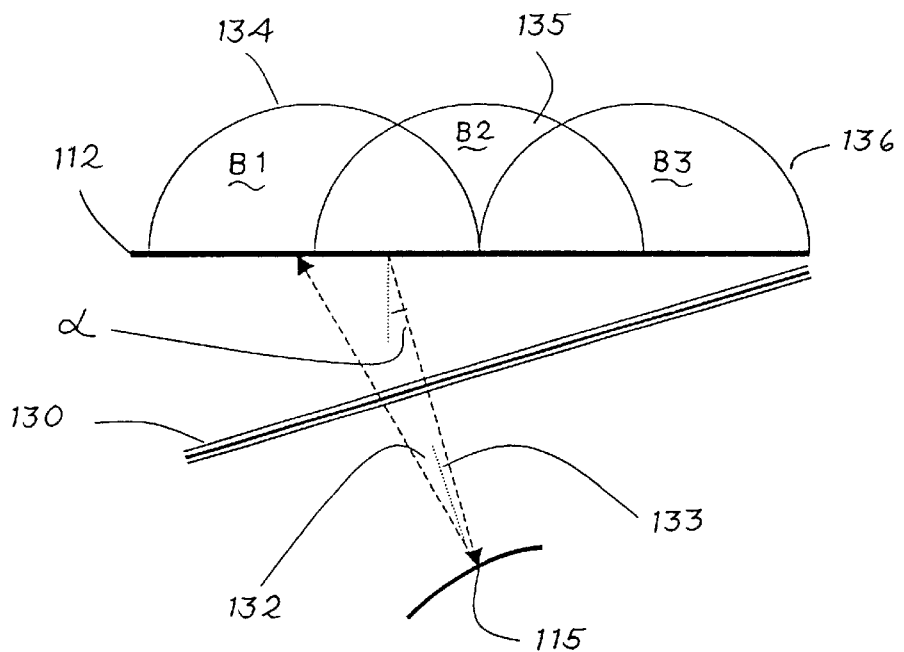
Figure 20:
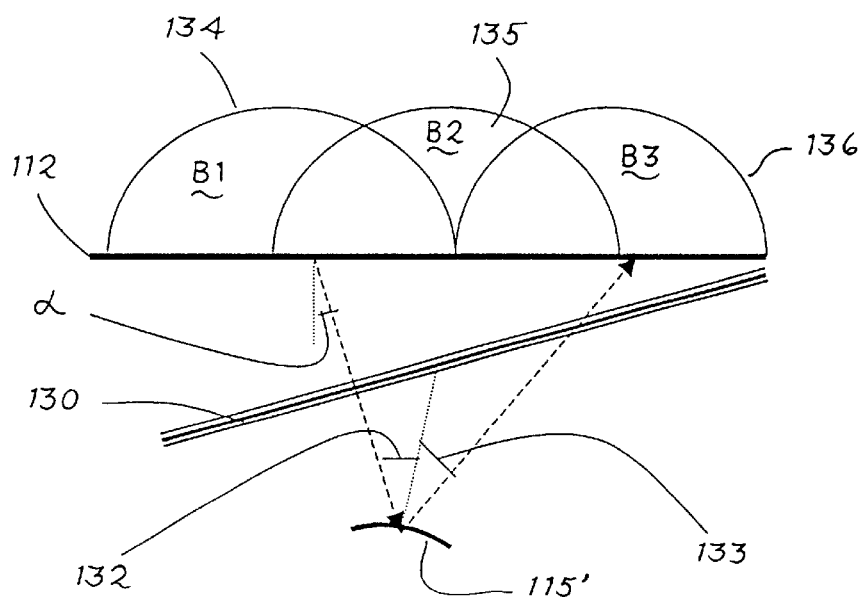

FIGS. 19 and 20 provide schematic representations of the array 112 and semi-planar targets 115,115' in two different orientations. In this example, the transmit pulse has a planar wavefront 130 that makes an angle $\alpha$, with respect to the array normal. Ultrasonic energy is reflected from the directional targets 115,115' such that the reflection angle 133 with the target's surface/line normal is equal to the incidence angle 132. In this example the available and addressable aperture of the array 112 for the particular target position for the targets 115,115' is divided into three receive sub-apertures 134, 135 and 136. Note that the available aperture is limited by the element factor, grating lobes and the physical aperture size. Therefore the available aperture is dependent on the target's depth and lateral position. The addressable aperture, on the other hand, is limited by the number of system acquisition channels. In this example each sub-aperture overlaps its adjacent sub-aperture by about 50%. Because the insonification is a plane wave, the reflected ultrasonic energy from directional targets strikes the array predominantly within one of the sub-apertures, the sub-aperture 134 in FIG. 19 and the sub-aperture 136 in FIG. 20.

Returning to FIG. 18, in block 162 the received echoes are beamformed over multiple partially overlapping receive sub-apertures, thereby forming multiple receive beams. With reference to FIGS. 19–20, the three sub-apertures 134, 135, 136 of this example are separately beamformed to provide three receive beams B1, B2, B3, respectively. In these examples the apodization type for the receive sub-apertures is Half-Circle. However, to compensate for the element factor or other acoustic attenuation effects the shape can be an asymmetric one and varied between the beams. Note that the receive beams B1 and B3 of the examples in the FIGS. 19 and 20, respectively, receive most of the reflected energy, while the other beams receive little or no energy from the respective directional targets.

Returning to FIG. 18, in block 164 each of the receive beams B1, B2, B3 is amplitude detected, and in block 166 at least some of the detected receive beams are combined in a spatial compounding operation. Any of the combining techniques described above in conjunction with the first preferred embodiment can be used.

The ultrasonic imaging system 110 of FIG. 17 can also be used to implement a modified form of the method of FIG. 18, in which two pulsed ultrasonic waves are sequentially transmitted toward the directional target, with the wavefronts oriented at different angles. FIGS. 21 and 22 show an example in which the wavefront 130 makes an angle $\alpha$ with the array normal, and the wavefront 140 makes an angle $-\alpha$. Compared to the single excitation example above, this technique doubles the range of angles that the imaging system is sensitive to. In this example, six separate receive beams are formed (three from each receive data set, each set corresponding to echoes from one of the wavefronts). All six of these receive beams are amplitude detected and combined.

Orthogonal codes can be used to code the transmit waves for different wavefronts. Then, they can be fired simultaneously rather than sequentially, which improves the frame rate. The receive data sets are decoded by the respective decoding filters to generate the two receive data sets, each corresponding to one of the wavefronts. Each data set is then used to beamform multiple receive beams with partially overlapping apertures. Alternatively the order of decoding and beamformation can be switched since they are linear functions (at least for small and moderate time-bandwidth products).

FIG. 23 shows another example, in which the planar wavefront 150 is oriented at an angle alpha equal to 0° with respect to the face of the transducer array 112.

The systems and methods of FIGS. 17–23 can readily be expanded to include receive arrays that are not co-linear. For example, the array 112 can be implemented as a curved array, or as a two-dimensional array. When a two-dimensional array is used, the various sub-apertures can be angled with respect to each other in the plane or face of the array.

In addition to the planar wavefronts illustrated in the drawings, non-planar waves can also be used. Note that to generate a laterally narrow-band response from a directional target that is located in a particular sample volume (resolution cell), the insonification need only be substantially planar or semi-planar, not precisely planar, and only within that particular sample volume, not in a big volume. The size of the sample volume here is determined by the main lobe volume of the receive point-spread function.

Among non-planar waves, weakly diverging and weakly focused waves are of particular interest. Compared to planar waves, weakly diverging waves increase the insonification area/volume per transmit excitation and therefore help further improve frame rate. This, however, compromises SNR and increase clutter levels. Weakly focused waves, on the other hand, improve SNR and reduce clutter levels while compromising frame rate. Insonification with these types of wavefronts may be considered to be substantially planar, or semi-planar, because the focused receive beam selects only the transmitted wave in the vicinity of the image point. For this reason, the transmit wavefront of an unfocused or weakly focused wave at a particular point of interest is effectively planar, regardless of its larger scale structure, and all such wavefronts will be referred to here as substantially planar.

Conclusion

Several imaging systems have been described that improve the imaging of directional targets, reduce speckle variance and address the temporal resolution loss and motion artifact issues that the conventional spatial compounding techniques face.

Many changes and modifications can be made to the preferred embodiments described above. For example, all of these embodiments can be adapted for use with three-dimensional images. In the case of pre-detection filters, anisotropic, three-dimensional, pre-detection filters can then be used. The combiner 28, 120 can operate to provide any desired non-linear function to the respective input images or beams. For example, the combiner can include a stored, non-linear map that provides an output signal level for any combination of the respective input signals.

As used herein, the term "image" is intended broadly to include an ultrasonic image made up of all or a part of a frame, whether in two- or three-dimensions, including an image segment.

The term "pre-detection" indicates that a beamforming process has formed a beam signal, but that the beam signal has not yet been amplitude detected.

The term "coupled with" is intended broadly to encompass both direct and indirect coupling. Thus, two elements are said to be coupled together, whether or not a third, unnamed element is interposed therebetween.

The term "set" is intended broadly to mean one or more.

The term "downstream" is intended to indicate subsequent in an information processing sense. Thus, a second element is said to be downstream of a first element when the second element operates on a signal after the signal has been operated on by the first element.

The term "beam" refers to a beamformed signal, and can include only a part of a scan line or only a part of a two- or three-dimensional region around a selected pixel or voxel.

The term "anisotropic spatial filter" is intended broadly to refer to filters that operate in either the spatial domain or the spatial frequency domain.

The foregoing detailed description has described only a few of the many forms that this invention can take. For this reason, this detailed description is intended broadly by way of illustration, and not limitation. It is only the following claims, including all equivalents, that are intended to define the scope of this invention.

What is claimed is:

1. A medical ultrasonic imaging method comprising:

(a) acquiring a beamformed image frame;

(b) filtering the beamformed image frame prior to amplitude detection with a filter bank, said filter bank generating a plurality of filtered images, each filtered image selectively responsive to directional targets oriented in a respective range of spatial directions;

(c) amplitude detecting the filtered images, thereby forming respective filtered detected images; and (d) combining at least some of the filtered detected images.

2. The method of claim 1 wherein the filter bank comprises at least one lateral filter.

3. The method of claim 1 wherein the filter bank comprises at least one two-dimensional filter.

4. The method of claim 1 wherein the filter bank comprises at least one three-dimensional filter.

5. The method of claim 1 wherein the beamformed image comprises a two-dimensional image.

6. The method of claim 1 wherein the beamformed image comprises a three-dimensional image.

7. The method of claim 1 wherein (d) comprises combining at least some of the filtered, detected images in log domain.

8. The method of claim 1 wherein (d) comprises combining at least some of the filtered, detected images in intensity domain.

9. The method of claim 1 wherein (d) comprises applying a non-linear function to at least one of the filtered, detected images.

10. The method of claim 1 wherein the filter bank in (b) varies as a function of range.

11. The method of claim 1 wherein the filter bank in (b) varies as a function of at least one of the azimuth and elevation axes.

12. A medical ultrasonic imaging system comprising:

a transducer;

a transmitter coupled with the transducer;

a receiver coupled with the transducer;

a anisotropic, spatial, pre-detection filter bank coupled with the receiver, said filter bank generating a plurality of filtered images, each filtered image selectively responsive to directional targets oriented in a respective range of spatial directions;

a set of detectors coupled with the filter bank downstream of the filter bank; and a combiner coupled with the set of detectors downstream of the set of detectors.

13. The invention of claim 12 wherein the combiner comprises a log domain combiner.

14. The invention of claim 12 wherein the combiner comprises an intensity domain combiner.

15. The invention of claim 12 wherein the combiner comprises a non-linear combiner.

16. A medical ultrasound imaging method comprising:

(a) transmitting a set of pulsed ultrasonic wavefronts toward a selected region, each said wavefront being substantially planar at the selected region;

(b) beamforming received echoes from each said wavefront over a plurality of partially overlapping receive sub-apertures, thereby forming a respective plurality of receive beams for said selected region, each receive beam associated with a respective sub-aperture;

(c) amplitude detecting each said receive beam, thereby forming respective detected receive beams; and (d) combining at least some of the detected receive beams.

17. The method of claim 16 wherein (a) comprises transmitting a first wavefront oriented at an angle alpha.

18. The method of claim 17 wherein (a) further comprises transmitting a second wavefront oriented at an angle-alpha.

19. The method of claim 16 wherein the transducer elements are included in a planar array.

20. The method of claim 16 wherein the transducer elements are included in a curved array.

21. The method of claim 16 wherein the transducer elements are included in a two-dimensional array.

22. The method of claim 16 wherein (d) comprises combining at least some of the detected receive beams in log domain.

23. The method of claim 16 wherein (d) comprises combining at least some of the detected receive beams in intensity domain.

24. The method of claim 16 wherein (d) comprises applying a non-linear function to at least one of the detected receive beams.

25. The method of claim 17 wherein alpha is substantially equal to zero.

26. The method of claim 16 wherein (b) comprises beamforming the received echoes in the frequency domain.

27. A medical ultrasonic imaging system comprising:

a transducer;

a transmitter coupled with the transducer;

a receiver coupled with the transducer;

an anisotropic, spatial, predetection filter bank coupled with the receiver, said filter bank comprising:
   a first anisotropic spatial filter responsive to an input signal from the receiver and operative to generate a first filtered signal selectively responsive to directional targets oriented in a first range of spatial directions;
   a subtractor responsive to the input signal and the first filtered signal and operative to generate a second filtered signal selectively responsive to directional targets oriented in a second range of spatial directions.

28. The invention of claim 27 further comprising:

a second anisotropic spatial filter responsive to the second filtered signal and operative to generate a third filtered signal selectively responsive to directional targets oriented in a third range of spatial directions.

29. The invention of claim 28 further comprising:

a second subtractor responsive to the second and third filtered signals and operative to generate a fourth filtered signal selectively responsive to directional targets oriented in a fourth range of spatial directions.

30. The invention of claim 28 wherein the second filter passes one of positive and negative frequency components of the second filtered signal and blocks the other of positive and negative frequency components of the second filtered signal.

31. The invention of claim 27 further comprising:

a set of detectors coupled with the filter bank downstream of the filter bank; and a combiner coupled with the set of detectors downsteam of the set of detectors.

32. A medical ultrasonic imaging system comprising:

a transducer;

a transmitter coupled with the transducer;

a receiver coupled with the transducer;

an anisotropic, spatial, predetection filter bank coupled with the receiver, said filter bank comprising:
   a rotator responsive to an input image from the receiver to rotate the imput image by a first angle, thereby generating a rotated input image;
   an anisotropic spatial filter responsive to the rotated input image and operative to generate a filtered, rotated input image selectively responsive to directional targets oriented in a selected range of spatial directions; and
   a counter rotator responsive to the filtered, rotated input image to counter rotate the filtered, rotated input image by an inverse of the first angle.

33. The invention of claim 32 further comprising means for successively setting the first angle at a plurality of different values.

34. The invention of claim 32 further comprising:

a set of detectors coupled with the filter bank downstream of the filter bank; and a combiner coupled with the set of detectors downsteam of the set of detectors.

* * * * *